United States Patent [19]

Brownlee

[11] Patent Number: 4,585,004

[45] Date of Patent: Apr. 29, 1986

[54] HEART PACING AND INTRACARDIAC ELECTROGRAM MONITORING SYSTEM AND ASSOCIATED METHOD

[75] Inventor: Robert R. Brownlee, Ormond Beach, Fla.

[73] Assignee: Cardiac Control Systems, Inc., Palm Coast, Fla.

[21] Appl. No.: 616,054

[22] Filed: Jun. 1, 1984

[51] Int. Cl.$^4$ .............................................. A61N 1/36
[52] U.S. Cl. ............................... 128/419 PT; 128/903
[58] Field of Search ...... 128/419 P, 419 PG, 419 PT, 128/642, 784–786, 903

[56] References Cited

U.S. PATENT DOCUMENTS

| | | |
|---|---|---|
| 3,662,759 | 5/1972 | Dabolt . |
| 3,825,015 | 7/1974 | Berkovits . |
| 3,977,411 | 8/1976 | Hughes, Jr. et al. ............ 128/419 P |
| 3,995,623 | 12/1976 | Blake et al. ...................... 128/419 P |
| 4,026,305 | 5/1977 | Brownlee et al. ............ 128/419 PT |
| 4,142,533 | 3/1979 | Brownlee et al. . |
| 4,355,642 | 10/1982 | Alferness . |
| 4,374,382 | 2/1983 | Markowitz . |
| 4,387,717 | 6/1983 | Brownlee et al. ............ 128/419 PG |
| 4,394,866 | 7/1983 | Hughes . |

FOREIGN PATENT DOCUMENTS 2026870 2/1980 United Kingdom ......... 128/419 PG

*Primary Examiner*—William E. Kamm
*Attorney, Agent, or Firm*—Kerkam, Stowell, Kondracki & Clarke

[57] ABSTRACT

A heart pacing and monitoring system includes a new lead system which, when used in conjunction with a telemetry-pacemaker system, permits the transmission of the complete intracardiac electrogram and is not adversely affected by pacemaker outputs or after potentials. Detecting ring electrodes are placed in both right atrium and ventricle in order to optimize electrogram (EGM) detection. Electrically separate from the pacing-sensing electrodes, the detecting electrodes are structurally part of a transvenously placed ventricular lead no larger than a conventional bipolar lead. The EGM telemetry system is also compatible with telephone monitoring systems. The present system is operative to detect and telemetrically record the entire normal and abnormal electrogram even in pacer dependent patients.

13 Claims, 4 Drawing Figures

HEART PACING AND INTRACARDIAC ELECTROGRAM MONITORING SYSTEM AND ASSOCIATED METHOD

BACKGROUND OF THE INVENTION

This invention relates to an implantable heart pacing and monitoring system. More specifically, this invention relates to a system which produces an intracardiac electrogram and transmits the electrogram to monitoring instruments external to the patient. Further, this invention relates to an associated method for heart pacing and monitoring.

The use of heart pacers, commonly called "pacemakers", is well known in the art. Such devices include a pulse generator which stimulates the patient's heart by use of one or more pacing-sensing electrodes.

The evaluation of pacer function is considered mandatory for the health and well being of the patient. As pacemaker or pacer longevity increases, better and more sophisticated follow-up methods have become available. The telemetric monitoring of such diverse pacemaker functions as output voltage and current, rate, end of life indication, refractory periods and delays are becoming common. The ordinary surface electrocardiogram is still relied upon to differentiate the arrhythmias produced by the pacemaker from abnormal pacemaker function. This task has become increasingly complex with the development of dual chamber and the so-called physiological pacemakers. The multiple modes of pacing and having pacers being "committed" and "non-committed" have produced a wide array of ecg (electrocardiograph) changes which can make interpretation of pacemaker function difficult. Monitoring has progressed from a simple lead II electrocardiogram to a minimum of six leads for ventricular pacing to a full 12 lead ecg for dual chamber pacers. Echocardiographs have even been required to aid in determination of capture in some difficult cases. All of these techniques are time consuming and expensive for the patient.

The ability of pacing electrodes to sense and detect normal intrinsic cardiac electrical activity is well known. These electrodes are adequate, in most instances, for the detection of the normal non-paced electrocardiogram. Telemetry systems incorporating such sensing systems have heretofore been used. Such systems cannot, however, be used to detect the electrocardiogram immediately following a stimuli originating from that electrode. The high output spike, after-potential, and electrode-tissue polarizations render the electrode blind to the induced electrocardiogram. Furthermore, since the sensing circuit gain is tuned for the relatively low voltages of the heart (3-4 mV for the atrium, 10-20 mV for the ventricle), the thousand-fold higher output levels produced by the pacemaker must be blocked from the sensing circuit by blanking and refractory periods so that the pacer is not disabled to subsequent electrial activity. In other words, the pacing-sensing electrodes are temporarily blinded in somewhat similar fashion to dark-adapted eyes being suddenly blinded by a very bright light. It is not even possible to try to determine a capture electrocardiogram until long after the intrinsic waveform has moved well away from the pacing spike. Therefore, a system which uses the same electrode for pacing, sensing, and telemetry may only generate a complete electrogram when the pacemaker is not pacing. This negates the use of a just one electrode telemetry-pacing system in all single chamber and any dual chamber pacer where both chambers may be paced.

The detection of the intracardiac electrogram by a single electrode separate from the pacing-sensing electrode is disclosed for example, in U.S. Pat. No. 4,387,717 issued June 14, 1983 to Robert R. Brownlee, Howard C. Hughes, Jr., Paul H. Neff, and G. Frank O. Tyers, entitled "Pacer Internal Cardiac Electrogram Sensing System", and this patent is hereby incorporated by reference. Although this system is capable of detecting the electrogram during both intrinsic and paced beats, it lacked the ability for high resolution electrogram detection from both chambers simultaneously. The single, separate electrode was used to pick-up both P and R waves.

The following incorporated by reference patents are further representative of other arrangements for heart pacing:

| U.S. Pat. No. | Inventor | Issuance Date |
| --- | --- | --- |
| 3,662,759 | Dabolt | May 16, 1972 |
| 3,825,015 | Berkovits | July 23, 1974 |
| 3,977,411 | Hughes, Jr. et al | Aug. 31, 1976 |
| 4,142,533 | Brownlee et al | Mar. 6, 1979 |
| 4,355,642 | Alferness | Oct. 26, 1982 |
| 4,374,382 | Markowitz | Feb. 15, 1983 |
| 4,394,866 | Hughes | Jul. 26, 1983 |

The Dabolt patent discloses a pacemaker which produces artifacts for detection upon a traditional EKG machine. These marker pulses indicate whether the pacemaker has sensed the normal intrinsic activity.

The Berkovits patent discloses pacing the heart through exposed ring electrodes. The electrodes are bipolar meaning that the rings in each of separate heart chambers are designed to be used as pairs, one ring serving as the cathode and other ring serving as the anode. The ring electrodes are used for atrium-ventricle sequential pacing.

The Hughes et al U.S. Pat. No. 3,977,411 describes a cardiac pacer system and method where an electrode with a relatively large surface area is used for sensing cardiac activity, and a second electrode in contact with the myocardium is used for applying the stimulator pulses to the heart. Both electrodes are unipolar, and the sensing electrode is used for controlling the pacemaker electronics and detecting R-wave activity.

The Brownlee et al U.S. Pat. No. 4,142,533 discloses a system for telemetering and monitoring the function of an implanted pacemaker. The telemetry is by digital signals.

The Alferness patent discloses a detecting electrode constructed for attachment to the surface of a patient's heart. This type of electrode would not normally be implanted through the vascular system, but instead would be implanted transthoracically. This electrode system would be used for looking at a very limited area of the myocardium (viz., area between the electrodes) to detect ventricle electrical activity.

The Markowitz patent discloses a pacer circuit including a telemetry system. The telemetry system generates a series of pulses which simply indicate whether an event has been detected by the pacemaker circuit and if the pacemaker circuit has responded to the event. The system uses the pacemaker's pacing-sensing electrodes for this detection.

The Hughes U.S. Pat. No. 4,394,866 discloses an S-A node helical lead for use with atrial pacemakers. The tip of the lead is placed at the area of the S-A node for optimal detection of the P-wave by the pacemaker and for generating the stimulating pulse or pacing through the same conductive member.

Although the discussed pacing systems have been generally useful, they are commonly subject to one or more of a number of problems or limitations in applicability.

The heretofore discussed designs have been unable to telemeter a reliable and complete intracardiac electrogram (EGM) during the pacing operation. Generally therefore, the examination of the pacer performance and capture still ultimately rely upon an external or surface electrocardiogram (EKG) which may be extremely difficult to monitor and interpret due to such factors as retrograde conduction, fusion, pseudo-fusion, and confusion concerning programmed settings.

OBJECTS AND SUMMARY OF THE INVENTION

Accordingly, it is an object of the present invention to provide a new and improved implantable human heart pacing and monitoring system.

Another object of the present invention is to provide a new and improved method for pacing and monitoring a human heart.

A more specific object of the present invention is to provide an implantable heart pacing and monitoring system which can sense the complete paced and non-paced intracardiac electrogram.

A further object of the present invention is to provide a heart pacing and monitoring system which can telemeter the intracardiac electrogram to external instruments.

A further object of the present invention is to provide an implantable data lead which will accurately detect an intracardiac electrogram.

Yet another object of the present invention is to provide an analog telemetry circuit which will accurately transmit an intracardiac electrogram.

The above and other objects of the present invention which will become apparent as the description proceeds are realized by an implantable human heart pacing and monitoring system comprising: an implantable housing; a heart pacer circuit within the housing; a first pacing-sensing electrode electrically connected to the pacer circuit; a telemetry circuit within the housing; an A-V data lead including a data wire electrically separate from the first pacing-sensing electrode and operable to feed a complete intracardiac electrogram to the telemetry circuit, the data wire connected to: (I) a detecting atrium ring electrode, and (II) a detecting ventricle ring electrode electrically connected to a common point as the atrium ring electrode; and a coil connected to the pacer circuit and the telemetry circuit and operable to transmit at least one pacer circuit function and the complete paced and non-paced intracardiac electrogram. The system may further comprise a second pacing-sensing electode connected to the pacer circuit and electrically separate from the data lead wire. The telemetry circuit is an analog circuit and the coil is operable to transmit the complete paced and non-paced intracardiac electrogram in an analog form. The A-V data lead includes insulation of segmented polyether polyurethane and the atrium and ventricle electrodes are made of platinum-irridium, elgiloy, carbon or other conductive biocompatible materials. Silicone or other flexible biocompatible insulating materials can be used for the insulation. The first pacing-sensing electrode is connected to a central pacing wire disposed in the A-V data lead. Alternately, the first pacing-sensing electrode is connected to a pacing wire in the A-V data lead along side of the data wire. Each of the ring electrodes has a contact area of 20 $mm^2$ to 100 $mm^2$ preferably 50 $mm^2$. The first pacing sensing electrode has a contact area of 8.0 $mm^2$ to 15.0 $mm^2$ preferably 10.0 $mm^2$.

The present invention further includes a method for pacing and monitoring a human heart, the steps comprising: implanting the implantable heart pacing and monitoring system described above within a patient with the atrium ring electrode in the patient's atrium for P-wave detection and the ventricle ring electrode in the patient's ventricle for R-wave detection; pacing the patient's heart by operation of the first pacing sensing electrode and the pacer circuit; and feeding a complete intracardiac electrogram from the ring electrodes to the telemetry circuit by way of the data wire. The method further comprises the steps of transmitting the intracardiac electrogram across the patient's skin by way of the coil, and receiving the intracardiac electrogram by an externally located telemetry probe connected to heart monitoring equipment. The telemetry circuit is an analog circuit and the intracardiac electrogram is transmitted in analog form. The system may further include a second pacing-sensing electrode connected to the pacer circuit and wherein the pacing is atrium-ventricle sequential pacing.

BRIEF DESCRIPTION OF THE DRAWINGS

The above and other features of the present invention will be more readily understood upon consideration of the following detailed description in conjunction with the accompanying drawings wherein like characters represent like parts through out the several views and in which.

DETAILED DESCRIPTION

Figure 1:
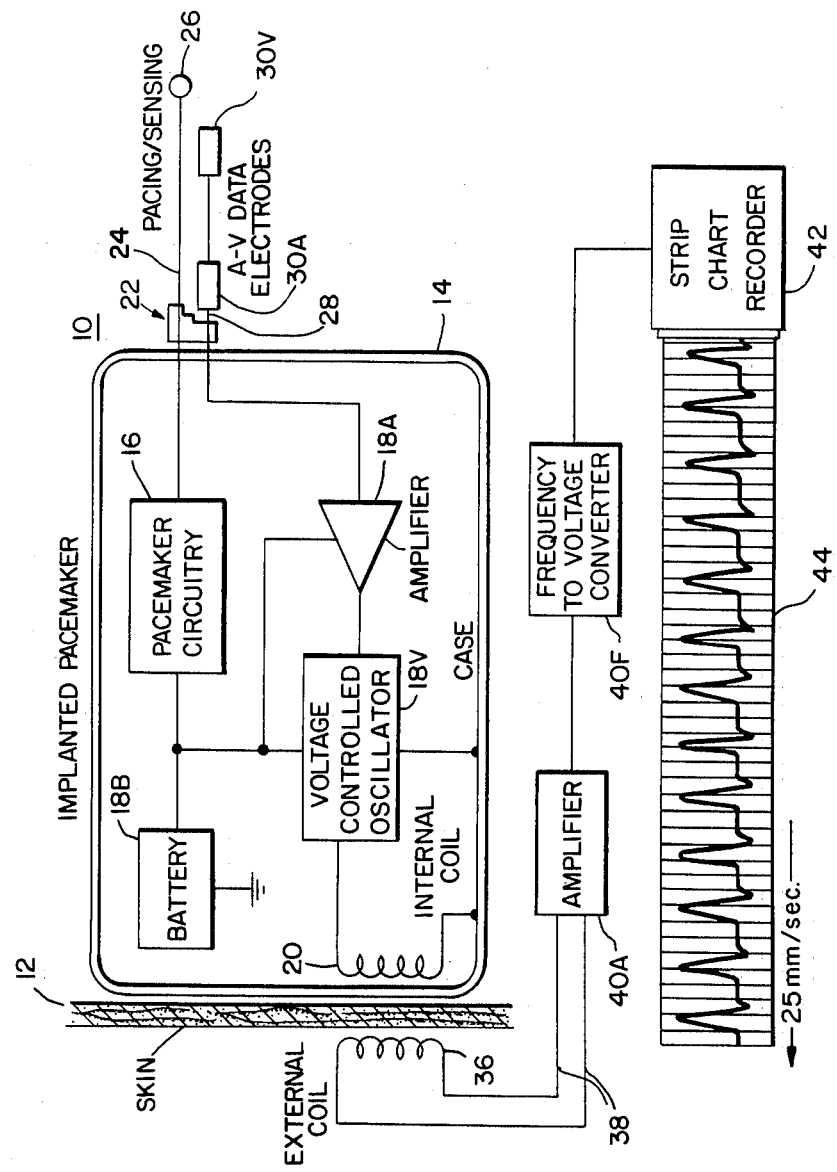
FIG. 1 shows a schematic representation of the present invention in conjunction with external heart monitoring equipment.

FIG. 1 shows a schematic representation of an implantable human heart pacing and monitoring system 10 according to the present invention. As illustrated, the system 10 is disposed under a patient's skin 12.

The system 10 includes an implantable housing 14 containing a heart pacer circuit 16 and an analog telemetry circuit comprising amplifier 18A and voltage controlled oscillator 18V, which is connected to a coil 20. The voltage controlled oscillator 18V or other form of voltage to frequency converter generates a frequency signal dependent on the voltage, the frequency signal is coupled to external coil 36 by way of the internal coil 20. A battery 18B powers the pacemaker system 10.

Extending from the housing 14 is an A-V (atrium-ventricle) data lead 22 including a pacing wire 24 connected to a pacing-sensing electrode 26 and a data wire 28 electrically separate from the pacing sensing electrode 26 and including a detecting atrium ring electrode 30A and a detecting ventricle ring electrode 30V electrically tied to a common point (data wire 28) as the atrium ring electrode.

Figure 4:
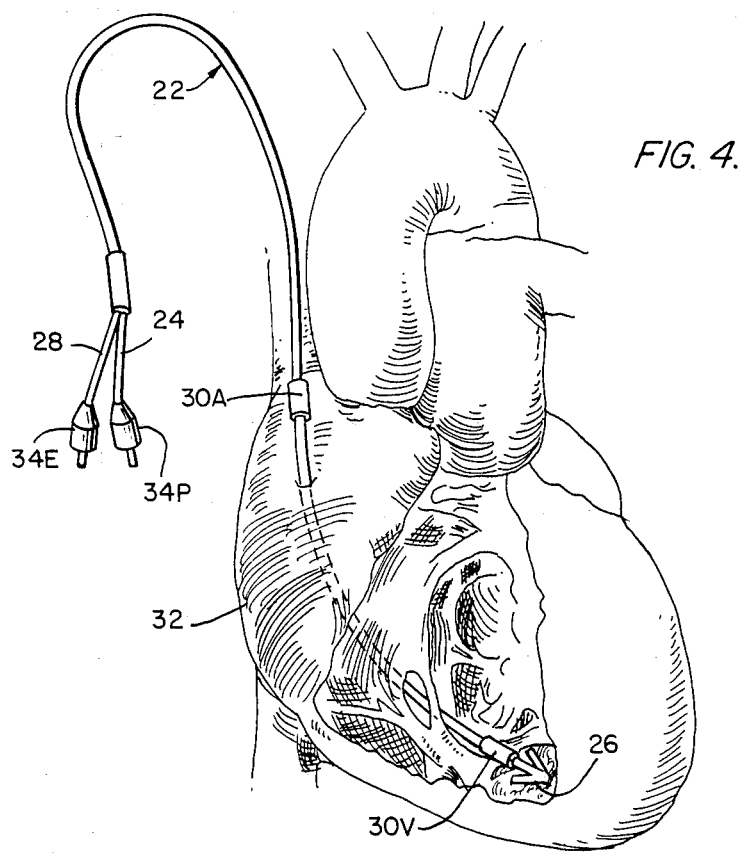
FIG. 4 shows the data lead system of the present invention installed within a patient's heart.

Continuing to consider FIG. 1, but also considering the perspective view of FIG. 4, the details of the A-V data lead will be discussed. As shown in FIG. 4, the data lead 22 is passed transvenously into the right ventricle such that the pacing-sensing electrode 26, situated at the tip of the data lead 22 will be lodged firmly in the apex of a patient's heart 32. The tip pacing-sensing electrode 26 is used for both pacemaker functions of pacing and sensing and constitutes a 10.0 mm$^2$ platinum-irridium contact area connected to the pacemaker circuitry 16 by wire 24. The sensing ring electrodes 30A and 30V each have 50 mm$^2$ of contact area of platimum-irridium and are tied electronically together to the common electrical point of wire 28. Other metals such as Elgiloy or carbon are also acceptable for electrodes 26, 30A, and 30V. The ring electrodes 30A and 30V are positioned along the body of the lead 22 such that the ventricle ring 30V is positioned approximately 1.0 cm from the tip electrode 26 for optimum R-wave detection. The atrium ring 30A is positioned 13.0 cm from the tip electrode 26 so that is lays in close proximity to the S-A node for P-wave detection. The distances may vary depending on the heart size. The lead 22 insulation is a segmented polyether polyurethane and is made so that the insulation material is bonded to the wires to produce a smooth, strong, thin (less than 2.3 mm diameter), low friction, biocompatible system. Silicone or other flexible biocompatible insulating materials could be used for the lead insulation. The tip electrode 26 is tined for fixation, although other methods can be used for fixation. Plugs 34P and 34E are respectively used to connect the pacing wire 24 and the electrogram data wire 28 to the housing 14 such that the pacing wire 24 is electrically connected to the pacemaker circuitry 16 and the electrogram data wire 28 is electrically connected to the analog telemetry circuit (18V and 18A). Electrodes 30V and 30A are unipolar and the pacemaker case 14 is the indifferent electrode. Because the jacks in which the plugs 34P and 34E are fitted are not a central part of the present invention, these jacks have not been shown in the drawings. Obviously, any of numerous electrical connection techniques could be used for connecting the wires 24 and 28 to the respective corresponding circuits 16 and 18A.

The pacemaker circuitry 16 may be realized by numerous different constructions well known in the art. Basically, this circuit may be similar to the pulse generator circuit 8 and associated control and monitoring circuits shown in FIG. 1 of the incorporated by reference Brownlee et al '717 patent. Additionally, a second or atrium sensing-pacing electrode similar to the pacing-sensing electrode 26 may also be used for sequential pacing as outlined in the Brownlee et al '717 patent.

Basically, the analog telemetry circuit of 18A and 18V receives the electrogram signal from electrogram data wire 28, amplifies it, and transmits it to coil 20 for transmission outside of the patient's skin 12.

As shown in FIG. 1, the electrogram signal transmitted by the internal coil 20 may be received by the telemetry probe or external coil 36. In addition to receiving the analog electrocardiogram signal, the telemetry probe 36 may receive other signals relating to the pacemaker functioning (battery voltage or numerous other functions).

The signals which are received by the telemetry probe 36 are fed by wires 38 into decode circuitry comprising amplifier 40A and frequency to voltage converter 40F which in turn is connected to the strip recorder 42. Circuitry connected to wires 38 may also be used to divide out or demultiplex various signals coming in on the wires 38, the analog electrogram signal being fed to the appropriate input of the recorder 42 to generate an electrogram tracing on the chart 44.

Testing and Results

Figure 2:
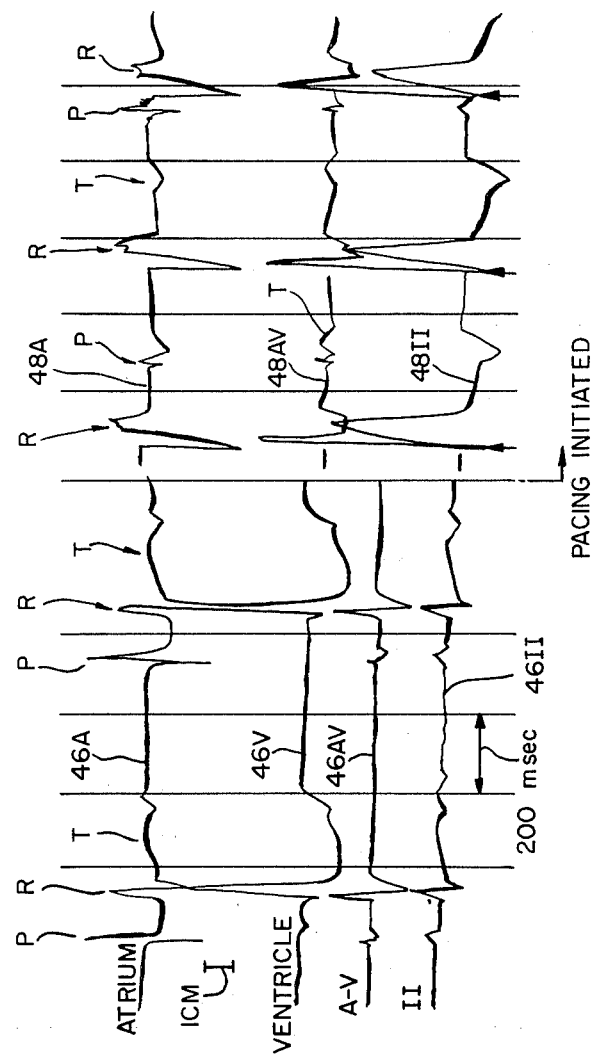
FIG. 2 shows a time chart illustrating various wave forms useful in understanding the present invention.
Figure 3:
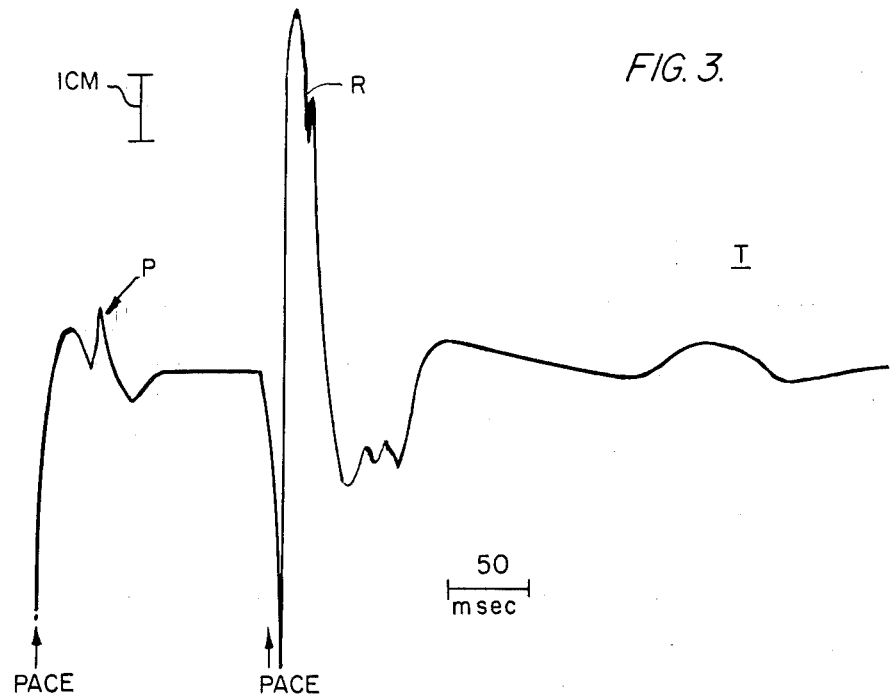
FIG. 3 shows an intracardiac electrogram as generated by the present invention.

Turning now to FIGS. 2 and 3, test results of the present invention will be discussed.

In testing the invention by acute studies, dogs (n=15) were anesthetized with pentobarbital, intubated and maintained on positive pressure ventilation. The right jugular vein was exposed and isolated 10 cm from the thoracic inlet. A right thoracotomy was done to visualize the heart. The A-V data lead 22 was passed transvenously into the right ventricle so that the lead tip was lodged firmly in the apex. Atrial J-leads were passed through the same vein and their tips were placed in the right atrium. The positions of both leads were confirmed by direct observation and palpation.

In chronic studes, eight dogs (35–40 lbs) were anesthetized and prepared for sterile surgery. The right jugular vein was isolated and the A-V data lead 22 was passed transvenously into the right ventricle under a fluoroscope.

Electrophysiological measurements were done similarly in all animals. An E for M, VR-6 Recorder was used for the electrogram (EGM) measurements. All measurements were done using a 50 cm$^2$ subcutaneous ground plate as the indifferent electrode. The EGM for the right ventricle was determined for the tip electrode in the unipolar mode. The EGM from the A-V Date Probe was examined separately, also in the unipolar mode. Continuous recordings were made at 100 mm/sec and triggered sweeps were photographed at 250–1000 mm/sec. Pacing thresholds were determined using a custom-designed square wave stimulator at five pulse durations from 0.1–1.0 msec. Threshold voltage and currents were determined using an oscilloscope. Electrograms were recorded from the A-V data lead during atrial, ventricular, and A-V sequential pacing as well as during sinus rhythm. In the chronic studies, the A-V data leads were connected to telemetrically monitored VVI pacemakers following operative electrophysiologic measurements.

The A-V data leads handled like an ordinary coaxial lead. With the guidewire in place, it passed easily through the venous system and into the right ventricle. The position of the tip was confirmed visually and by palpation in the acute animals. Stability and lodgement were similar to other tined ventricular leads. The ability of the tip to detect R-waves and to pace the heart were identical to other unipolar ventricular leads of similar surface area. Acute R-wave potentials were 26±6.7 mV with a duration of 9.8±4.2 msec. Pacing thresholds are shown in Table I.

TABLE I

| Pacing Thresholds for the Tip Electrode of the A-V Data Lead | | | | | |
|---|---|---|---|---|---|
| | 0.1 | 0.2 | 0.5 | 0.8 | 1.0 |
| Volts | 0.84 ± 0.17 | 0.58 ± 0.20 | 0.36 ± 0.23 | 0.24 ± 0.3 | 0.19 ± 0.02 |
| Milli- | 1.68 ± 0.45 | 1.10 ± | 0.60 ± 0.40 | 0.39 ± | 0.30 ± 0.17 |

TABLE I-continued

| Pacing Thresholds for the Tip Electrode of the A-V Data Lead | | | | | |
| --- | --- | --- | --- | --- | --- |
| | 0.1 | 0.2 | 0.5 | 0.8 | 1.0 |
| amps | | 0.48 | | 0.21 | |

Means ± standard deviation

Examination of the EGM detected from the A-V ring electrodes 30A and 30V (46AV) shows that it was similar in configuration to the lead II EGM (46II), but had a 5-6 times greater amplitude (FIG. 2). The lead II (46II) signal is the electrocardiogram tracing derived from a peripheral ECG (i.e., paste-on external electrodes). When compared to the EGM taken individually from the atrial (signal 46A) and ventricular (signal 46V) leads, there was a 25-50 percent attenuation of the signal. The scale is 2 mV/cm for 46A, 5 mV/cm for 46V and 46AV and 1 mV/cm for 46II in FIG. 2.

After pacing was initiated, the EGM could not be detected on the ventricular lead doing the pacing because of the pacer spike and after-potentials. It is therefore not shown. Detection of the EGM (48AV) from the A-V Data probes, however, was easily visible regardless of pacing site (FIG. 2). In comparison to the ECG, the individual waveforms were more easily recognizable by use of the present invention. In lead II, the P-waves were often obscured by T-waves (FIG. 2, 1st paced complex) and R-waves as atrial depolarization walked through the ecg. Similarly, the P-wave from the atrial lead EGM, tended to obscure the T-wave during ventricular pacing. In contrast, the A-V Data Lead EGM always detected clear distinct individual waveforms (P-, R- and T-waves).

During atrial pacing, the atrial tip electrode detected an entirely satisfactory R-wave (48A). The signals 46A and 48A are from a separate atrial lead such as a standard J-lead or an atrial helix lead. The atrial lead (or a ventricle lead) could be used for the telemetry during nonpacing. If atrial pacing was being used, we would not be able to look at it telemetrically. The P-waves detected by the atrial electrode, however, were of such low amplitude that determination of atrial capture was not always possible. With the A-V Data Lead, there was excellent differentiation of waveforms. The pacer artifact was clear and P-waves were distinct. Accurate measurements of stimulus to P-waves and P- R intervals could be made. When A-V sequential pacing was initiated, the EGM from both the atrial and ventricular tip leads were not detectable due to the relatively high amplitude spikes and afterpotentials. With the A-V Data Lead, P-, R-, and T-waves were readily detectable following the pacemaker stimuli, as were the other electrophysiologic parameters that are normally measured (FIG. 3).

In experiments on dogs, the present invention was tested with telemetry unit functioning properly while implanted. Simply by placing an external telemetry coil in the vicinity of the internal telemetry system, intrinsic and paced intracardiac EGM's were easily detectable (FIG. 1). P-, R- and T-waves, premature beats, arrhythmias and EGM intervals were all easily identifiable. In one animal that had previously undergone chest surgery, a myocarditis and its associated arrhythmias were detected with this system before obvious clinical signs had occurred. There have been no lead or telemetry related failures.

Some cancellation of the signal, primarily the R-wave, does occur due to electrode loading and detection of far field signals on the ring in the nonactive chamber. This resulted in the 25-50% reduction in R-wave amplitude as compared to a single ring.

The A-V data lead 22 is capable of detecting and transmitting the entire EGM from both chambers of the heart. The pacing EGM, whether it is single or dual chamber, is equally as clear and straightforward as is the intrinsic EGM. The pacer output spikes are clear and these are followed by distinct P- or R-waves. The T-wave and P-waves are not obscured by pacing or other electrical events occurring in the other chamber. Capture, fusion, pseudofusion, and non-capture are all readily indentified. Similarly, the measurement of all electrophysiological intervals is possible.

The size (less than 2.3 mm diameter) and handling characteristics of this lead are similar to those of the standard bipolar leads. The polyurethane assures long-term biocompatibility and stability. When used in conjunction with telemetry pacing systems, this lead will add significantly to the long-term and diagnostic ease in the pacemaker patient. Clear, concise EGM recordings will be available by transtelephonic monitoring systems (FIG. 1).

Although various specific embodiments and details have been disclosed herein, it is to be readily understood that these are for illustrative purposes only. Various modifications and adaptations will be readily apparent to those of ordinary skill in the art. Accordingly, the scope of the present invention should be determined by reference to the claims appended hereto.

What is claimed is:

1. An implantable human heart pacing and monitoring system comprising:
   (a) an implantable housing;
   (b) a heart pacer circuit within said housing;
   (c) a first pacing-sensing electrode connected to said pacer circuit;
   (d) a telemetry circuit within said housing;
   (e) an A-V data lead connected to said telemetry circuit and including a data wire electrically separate from said first pacing-sensing electrode and:
      (I) a detecting atrium ring electrode, and
      (II) a detecting ventricle ring electrode, wherin said atrium ring and said ventricular ring are electrically tied in common to said data wire, and said data wire is operable to feed a complete intracardiac electrogram to said telementry circuit; and
   (f) a coil connected to said telemetry circuit and operable to transmit at least one pacer circuit function and the complete paced and nonpaced intracardiac electrogram.

2. The implantable human heart pacing and monitoring system of claim 1 wherein said telemetry circuit is an analog circuit and said coil is operable to transmit the complete paced and nonpaced intracardiac electrogram in analog form.

3. The implantable human heart pacing and monitoring system of claim 2 wherein said A-V data lead includes insulation of segmented polyether polyurethane and said atrium and ventricle electrodes are made of platinum-irridium.

4. The implantable human heart pacing and monitoring system of claim 2 further comprising a pacing wire in said A-V data lead along side of said data wire and connected to said first pacing-sensing electrode.

5. The implantable human heart pacing and monitoring system of claim 4 wherein said first pacing-sensing electrode has a contact area of 8.0 mm² to 15.0 mm².

6. The implantable human heart pacing and monitoring system of claim 2 wherein each of said ring electrodes has a contact area of 20 mm² to 100 mm².

7. The implantable human heart pacing and monitoring system of claim 2 wherein said analog telemetry circuit includes an amplifier and a voltage controlled oscillator, said amplifier connected to said voltage controlled oscillator, and wherein said coil is connected to said voltage controlled oscillator.

8. A method for pacing and monitoring a human heart, the steps comprising:
  (a) implanting an implantable heart pacing and monitoring system within a patient, said system including an implantable housing, a heart pacer circuit within said housing, a first pacing-sensing electrode connected to said pacer circuit, a telemetry circuit within said housing, an A-V data lead including a data wire electrically separate from said first pacing-sensing electrode and:
    (I) a detecting atrium ring electrode, and
    (II) a detecting ventricle ring electrode, said atrium ring and said ventricular ring being electrically tied in common to said data wire; and
    a coil connected to said telemetry circuit, said system being implanted with said atrium ring electrode in the patient's atrium for P-wave detection, and said ventricle ring electrode in the patient's ventricle for R-wave detection;
  (b) pacing the patient's heart by operation of said first pacing-sensing electrode and said pacer circuit;
  (c) feeding a complete intracardiac electrogram from said ring electrodes to said telemetry circuit by said data wire;
  (d) transmitting said intracardiac electrogram across the patient's skin by way of said coil; and
  (e) receiving said intracardiac electrogram by an externally located telemetry probe connected to heart monitoring equipment.

9. The method of claim 8 wherein said telemetry circuit is an analog circuit and said step of transmitting said intracardiac electrogram is analog transmission.

10. The method of claim 8 wherein said A-V data lead used in the method includes insulation of segmented polyether polyurethane and said atrium and ventricle electrodes are made of platinum-irridium.

11. The method of claim 8 wherein said system used for accomplishing the method includes a pacing wire in said A-V data lead along side of said data wire, said pacing wire connected to said first pacing-sensing electrode.

12. The method of claim 8 wherein each of said ring electrodes used in the method has a contact area of 20 mm² to 100 mm².

13. The method of claim 8 wherein said first pacing-sensing electrode used in the method has a contact area of 8.0 mm² to 15.0 mm².

* * * * *